US009909967B2

(12) United States Patent
McBrien et al.

(10) Patent No.: US 9,909,967 B2
(45) Date of Patent: Mar. 6, 2018

(54) FUEL DENSITY DETERMINATION

(71) Applicant: Simmonds Precision Products, Inc., Vergennes, VT (US)

(72) Inventors: Gary M. McBrien, S. Glastonbury, CT (US); David H. Crowne, Weybridge, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 708 days.

(21) Appl. No.: 14/529,489

(22) Filed: Oct. 31, 2014

(65) Prior Publication Data
US 2016/0123860 A1 May 5, 2016

(51) Int. Cl.
*G01N 31/00* (2006.01)
*G01N 9/00* (2006.01)
*G01F 1/00* (2006.01)
*G01M 15/14* (2006.01)
*G01N 27/22* (2006.01)
*G01N 33/22* (2006.01)
*G01F 1/86* (2006.01)
*G01F 25/00* (2006.01)

(52) U.S. Cl.
CPC ............... *G01N 9/00* (2013.01); *G01F 1/00* (2013.01); *G01F 1/86* (2013.01); *G01F 25/0007* (2013.01); *G01M 15/14* (2013.01); *G01N 27/221* (2013.01); *G01N 33/22* (2013.01); *G01N 27/226* (2013.01)

(58) Field of Classification Search
CPC ...... G01F 23/266; G01F 23/14; G01F 23/263; B64D 37/005
See application file for complete search history.

(56) References Cited

U.S. PATENT DOCUMENTS

| 3,635,084 | A | 1/1972 | Lamphere et al. | |
|---|---|---|---|---|
| 3,739,635 | A | 6/1973 | Stuart | |
| 4,258,422 | A * | 3/1981 | Dougherty | G01F 17/00 701/123 |
| 4,262,531 | A | 4/1981 | Hewitt et al. | |
| 5,265,460 | A | 11/1993 | Ellinger et al. | |
| 8,281,655 | B2 * | 10/2012 | Bahorich | G01F 23/266 73/304 C |
| 8,515,694 | B1 | 8/2013 | Orloff et al. | |
| 2009/0099794 | A1 * | 4/2009 | Boulanger | G01F 15/022 702/47 |
| 2012/0260731 | A1 * | 10/2012 | Austerlitz | G01F 23/263 73/32 R |

FOREIGN PATENT DOCUMENTS

EP 2330393 B1 4/2013

OTHER PUBLICATIONS

Partial European Search Report for EP Application No. 15192089.9, dated Apr. 6, 2016, 7 pages.

* cited by examiner

*Primary Examiner* — Elias Desta
(74) *Attorney, Agent, or Firm* — Kinney & Lange, P.A.

(57) ABSTRACT

A method for accurately determining a density of a fuel includes obtaining dielectric constant versus density characteristics of the fuel at a first location and measuring a dielectric constant of the fuel at a second location. The environmental conditions at the second location differ from environmental conditions at the first location. Density of the fuel at the second location is inferred using the dielectric constant of the fuel at the second location and the dielectric constant versus density characteristics of the fuel at the first location.

15 Claims, 4 Drawing Sheets

FUEL DENSITY DETERMINATION

BACKGROUND

The present embodiments relate generally to fluid-gauging assemblies and methods, and more particularly to fluid-gauging assemblies and methods for determining properties of fuel used in a gas turbine engine.

In one exemplary application, a gas turbine engine can be used on an aircraft. In aircraft engine control, it can be necessary to know a value of a mass flow of fuel due to mass flow's direct effect on engine thrust. Prior fuel gauging techniques have obtained fuel mass flow values using moving components within the engine. For example, two impellers connected by a shaft with a known spring constant have been used to find fuel mass flow given the proportional relation between torque on the shaft (and thus impeller angular displacement) and fuel mass flow. However, fuel-gauging techniques which utilize moving components are undesirable.

Fuel mass flow is equal to the product of fuel volumetric flow and fuel density. Fuel volumetric flow is readily obtained using known techniques. Thus, an accurate measurement of fuel density can yield fuel mass flow. Prior fuel gauging techniques have attempted to accurately determine fuel density by either directly measuring fuel density in a fuel tank external to the engine using some form of a densitometer, or measuring a dielectric constant of the fuel in the fuel tank external to the engine and then deducing fuel density using this measured dielectric constant in the fuel tank. However, such techniques do not provide an accurate enough measurement of fuel density to allow for precise, economical aircraft engine control.

SUMMARY

One embodiment includes a method for accurately determining a density of a fuel. The method includes obtaining dielectric constant versus density characteristics of the fuel at a first location and measuring a dielectric constant of the fuel at a second location. The environmental conditions at the second location differ from environmental conditions at the first location. Density of the fuel at the second location is inferred using the dielectric constant of the fuel at the second location and the dielectric constant versus density characteristics of the fuel at the first location.

Another embodiment includes an assembly used for determining a density of a fuel. The assembly includes a fuel line through which a fuel is passed and located at least partially within an engine, a fuel metering valve located within the fuel line and configured to receive the fuel through a first end and dispel the fuel through a second end, and a multi-plate capacitor device located within the fuel line through which the fuel passes. The device includes a first current sensing electrode plate, a second voltage driven electrode plate configured concentrically around the first plate, and an insulating material configured concentrically between the first plate and the second plate. The insulating material is present in an angular range between the first plate and the second plate less than 360° such that at least one gap is defined radially between the first plate and the second plate and along an axial distance of the first plate and the second plate. The at least one gap receives fuel at an upstream end and dispels fuel at a downstream end such that a first measurement of capacitance of the fuel can be obtained across the at least one gap.

Figure 1A:
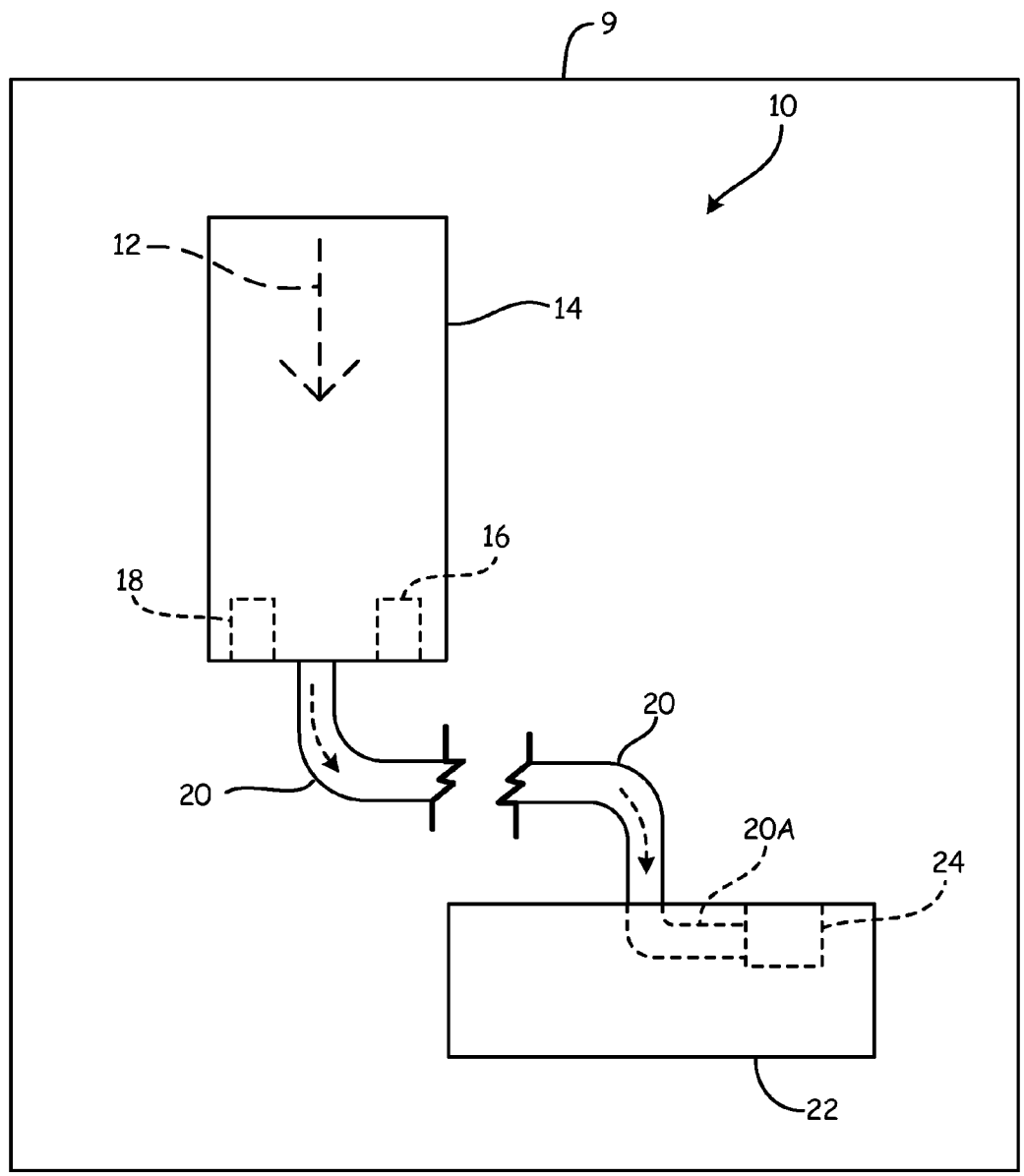
FIG. 1A is a schematic diagram of an assembly on an aircraft for determining a density of a fuel.

While the above-identified drawing figures set forth multiple embodiments of the invention, other embodiments are also contemplated. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features and components not specifically shown in the drawings.

DETAILED DESCRIPTION

The present embodiments provide assemblies and methods for accurately determining a density of a fuel. FIG. 1A is a schematic diagram of an aircraft 9 which includes an assembly 10 for accurately determining a density of fuel 12.

Assembly 10 includes fuel 12 which is stored in fuel tank 14. In one embodiment, fuel 12 can be, for example, a kerosene-based or kerosene-like fuel such as Jet A, Jet A1, Jet B, JP 4, JP 5, or JP 8, with or without additives such as stabilizers, etc. Fuel tank 14 is supplied with fuel 12 and serves to store fuel 12. In the illustrated embodiment, disposed inside of fuel tank 14 are density sensor 16 and dielectric sensor 18. As shown, density sensor 16 and dielectric sensor 18 are mounted on a bottom of fuel tank 14 such that these sensors 16 and 18 are generally fully immersed in fuel 12 regardless of whether a volume of fuel tank 14 is near full or near empty of fuel 12. However, in other embodiments sensors 16 and 18 can be mounted at least partially within fuel tank 14 at various other locations within fuel tank 14. Density sensor 16 can be, for example, a form of densitometer or any other device suitable for accurately measuring a density of fuel 12 within fuel tank 14. Dielectric sensor 18 can be, for example, a capacitor or any other device suitable for accurately measuring a dielectric constant (i.e. relative permittivity) of fuel 12 (i.e. where fuel 12 is the dielectric and the dielectric constant is relative to air).

Assembly 10 also includes fuel line 20, which is in fluid communication with both fuel tank 14 on one end and engine 22, on another end. Fuel line 20 serves to communicate fuel 12 from fuel tank 14 to engine 22. In one exemplary application, engine 22 is a gas turbine engine and can be mounted to aircraft 9 for powering and propelling aircraft 9. A portion 20A of fuel line 20 is within engine 22 and in fluid communication with combustor 24. Within combustor 24, fuel 12 is mixed with compressed air and ignited producing hot combustion gasses from which engine 22 extracts energy. Environmental conditions within engine 22, and thus environmental conditions at portion 20A of fuel line 20, differ from environmental conditions external to engine 22, such as within fuel tank 14. For instance, both a temperature and a pressure within engine 22 can be significantly greater than a temperature and pressure external to engine 22, such as within fuel tank 14. Additionally, operating conditions within engine 22 can vary at different times resulting in different environmental conditions, such as temperature and pressure, within engine 22 at a given time. Thus, as fuel 12 is communicated throughout assembly 10 fuel 12 will be subject to different temperatures and pressures.

Some prior assemblies and methods for determining a density of fuel 12 have utilized only density sensor 16 (and not dielectric sensor 18) within fuel tank 14. However, because fuel 12 will be subject to varying temperatures and pressures within assembly 10, a density of fuel 12 will vary throughout assembly 10. In fact, fuel 12 density can vary with temperature more than 25% over the typical operating range of most gas turbine engines 22. Consequently, a measurement of the density of fuel 12 using density sensor 16 within fuel tank 14 will not provide an accurate measurement of the density of fuel 12 at other assembly 10 locations, such as portion 20A of fuel line 20.

Other prior assemblies and methods for determining a density of fuel 12 have utilized dielectric sensor 18 to measure a dielectric constant of fuel 12 within fuel tank 14. As known to those in the art of fuel-gauging, a relationship between the dielectric constant of fuel 12 and density of fuel 12 is defined by the expression:

$$D = \frac{K-1}{A(K-1)+B} \tag{I}$$

where D is the density of fuel 12, K is the dielectric constant of fuel 12, and A and B are constants based on the type of fuel 12 (e.g. Jet A). However, because fuel 12 can be subject to different environmental conditions (e.g., different temperatures and pressures) within assembly 10, the dielectric constant of fuel 12 will vary throughout assembly 10. As a result, a measured dielectric constant of fuel 12 within fuel tank 14, for example, will not provide an accurate measurement of a dielectric constant of fuel 12 at other locations within assembly 10 which are exposed to different environmental conditions, such as at portion 20A. Therefore, measuring dielectric constant of fuel 12 at a first location within assembly 10 and using the expression to obtain a value of the density of fuel 12 at the first location will not provide an accurate value for the density of fuel 12 at a second location subject to different environmental conditions.

To further complicate matters, a particular type of fuel 12 (e.g. Jet A) is not consistent from sample to sample, and therefore the dielectric properties of that particular type of fuel 12 are not consistent (i.e. Jet A, for example, can have two different dielectric constant values at the same temperature). This inconsistency within a single type of fuel 12 is due to the fact that the proportions of olefin, paraffin, napthene, and aromatic, hydrocarbons which make up fuel 12, are not strictly controlled and indeed vary according to the geological source of the oil, local refining practices, and the type of fuel 12 being produced. As a result, a particular type of fuel 12 supplied to fuel tank 14 at one location can have dielectric properties which differ from that same particular type of fuel supplied to fuel tank 14 at a second location. Furthermore, in many cases the same type of fuel 12 from two different locations can end up mixed together inside fuel tank 14. Thus, using the dielectric constant of fuel 12 measured in fuel tank 14 does not provide an accurate calculation of fuel 12 density.

Such inaccuracies in the measurement of the density of fuel 12 can lead to, among others, inefficiencies in control of engine 22. The present embodiments provide assemblies and methods for accurately determining the density of fuel 12, and in particular accurately determining the density of fuel 12 at a location where the value of the density of fuel 12 is most useful in engine control.

Figure 1B:
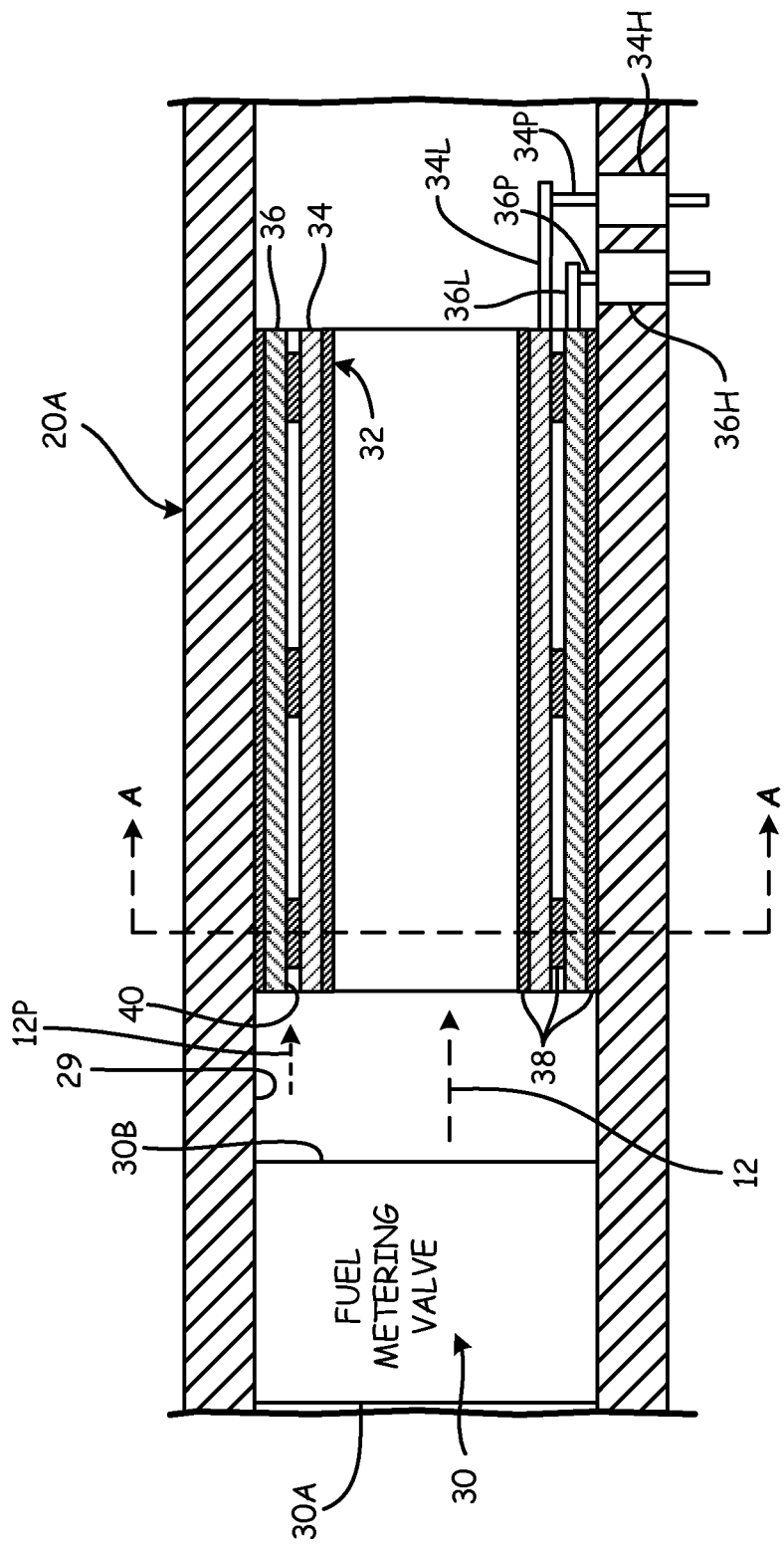
FIG. 1B is a cross-sectional view of a portion of a fuel line of the assembly of FIG. 1A with a metering valve and a multi-plate capacitor device.
Figure 1C:
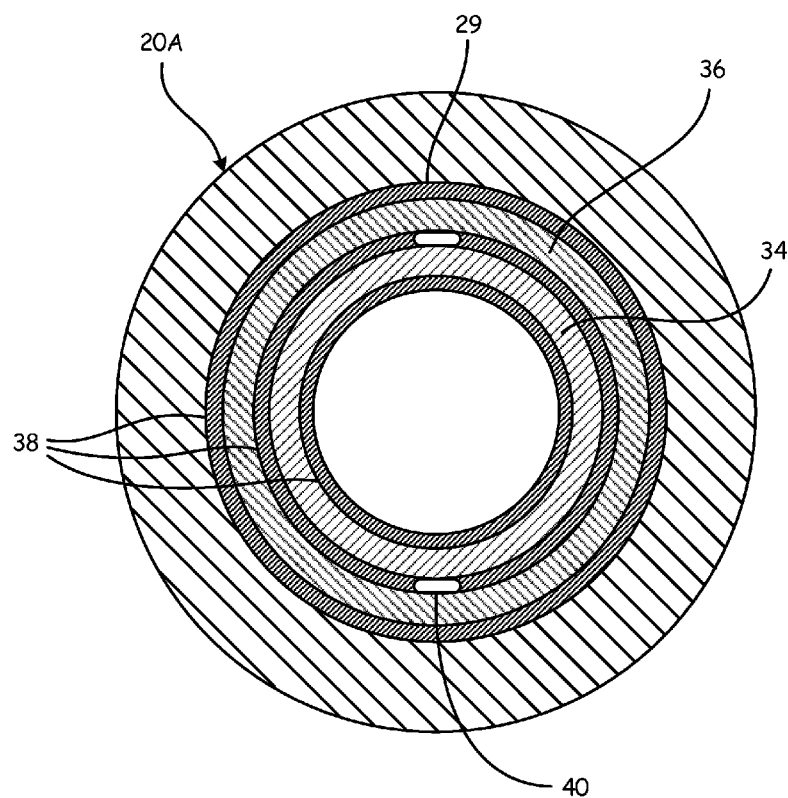
FIG. 1C is a cross-sectional view of the portion of the fuel line of FIG. 1B taken along line A-A.

FIGS. 1B and 1C illustrate detailed views of portion 20A of fuel line 20. FIG. 1B illustrates a cross-sectional view of portion 20A. FIG. 1C shows a cross-sectional view of portion 20A taken along line A-A of FIG. 1B.

As described previously, portion 20A is located within engine 22. Portion 20A defines fuel passage 29 through which fuel 12 flows. Included within portion 20A are fuel metering valve 30 (shown schematically) and multi-plate capacitor device 32. Metering valve 30 has a first end 30A on an upstream end of metering valve 30 and a second end 30B on a downstream end of metering valve 30. Metering valve 30 can be utilized to measure a volumetric flow of fuel 12 as is known in the art.

Capacitor device 32 includes first current sensing electrode plate 34 and second voltage driven electrode plate 36 configured concentrically around first plate 34. Plate 34 is in communication with connecting lead 34L, which is joined to header pin 34P which passes through glass header 34H disposed in a wall of portion 20A. Plate 36 is in communication with connecting lead 36L, which is joined to header pin 36P which passes through glass header 36H disposed in the wall of portion 20A. Insulating material 38 is disposed concentrically between fuel passage 29 and second plate 36, second plate 36 and first plate 34, and first plate 34 and fuel 12 passing through passage 29. Insulating material 38 is present at an angular range between first plate 34 and second plate 36 less than 360°, such that a gap or fuel entry 40 between first plate 34 and second plate 36 is defined both radially between plates 34 and 36 and axially along a distance of plates 34 and 36.

Capacitor device 32 functions to measure a capacitance of fuel 12, and thus a dielectric constant of fuel 12 at portion 20A. Fuel 12 enters through end 30A of metering valve 30 and is dispelled out end 30B. A majority of fuel 12 then passes through a center of fuel passage 29. However, a portion 12P of fuel 12 from end 30B flows into an upstream end of gap or fuel entry 40. Gap 40 is sized to have a cross-sectional area at any axial location along gap 40 large enough to allow debris or particulate normally present within fuel 12P to pass through gap 40 without causing blockage of gap 40. Yet, gap 40 is sized to have a cross-sectional area small enough to slow down a flow of fuel 12P passing through gap 40, relative to a flow of fuel 12 passing through a center of fuel passage 29 and bypassing gap 40. As fuel 12P passes through gap 40, fuel 12P is in contact with plate 34 on one side and plate 36 on another side such that fuel 12P serves as the dielectric allowing a capacitance of fuel 12P to be measured. This measured capacitance of fuel 12P within portion 20A can then be used to find the dielectric constant of fuel 12 (relative to air) at portion 20A. Fuel 12P is then dispelled at a downstream end of gap 40 where it merges with fuel 12 passing through the center of fuel passage 29. All fuel 12 can then be passed, for example, to combustor 24.

The described configuration of device 32 provides particular benefits. The concentric configuration of plates 34 and 36 allows device 32 to obtain a greater capacitive response while reducing an area taken up by plates 34 and 36 on an upstream end such that fluidic impedance on fuel 12 flowing through the center of fuel passage 29 is minimized. As compared to device 32, prior parallel electrode plate capacitors generate less capacitive response and create more impedance to the flow of fuel 12.

Figure 2:
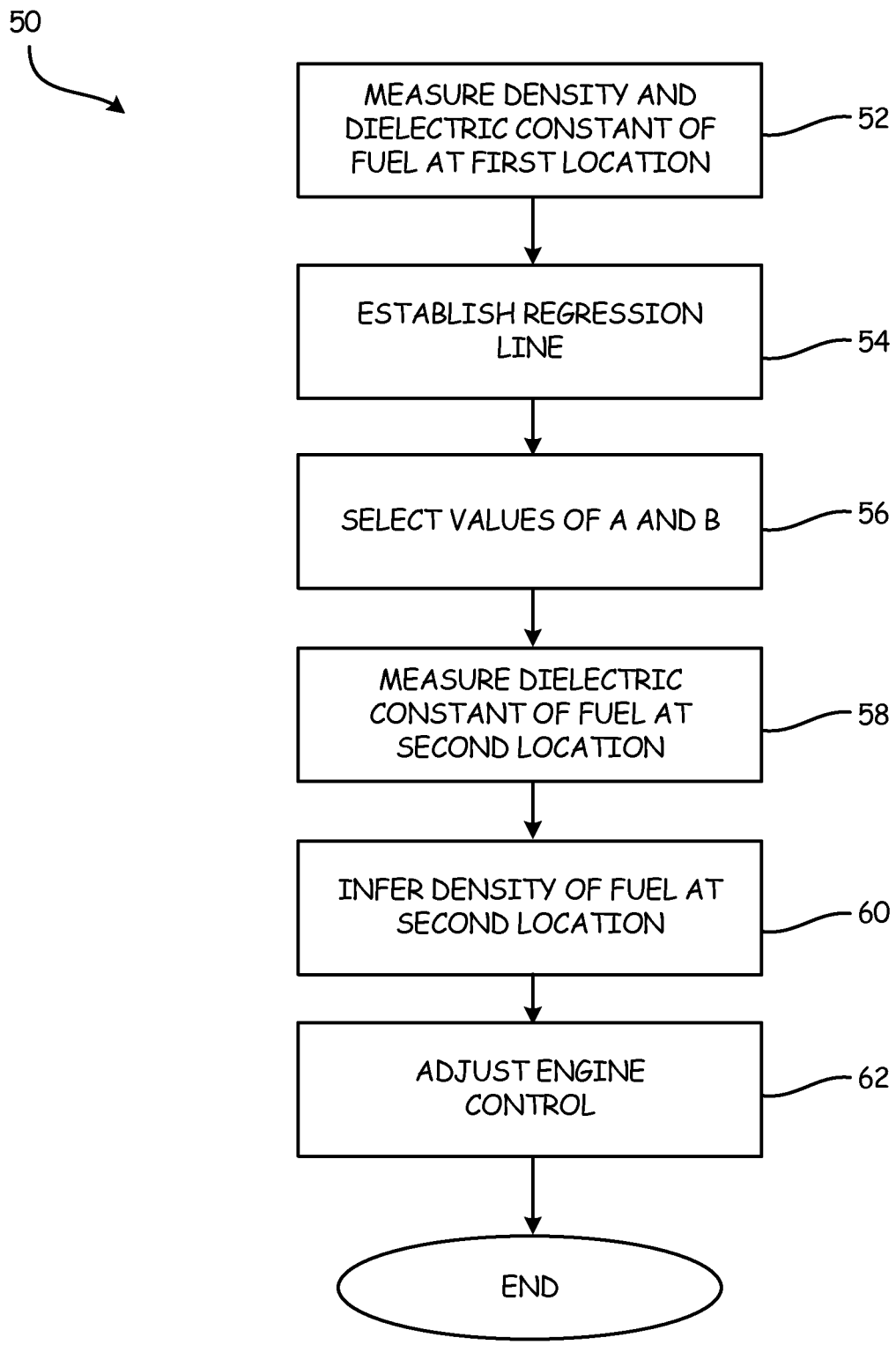
FIG. 2 is a flow diagram illustrating a method for accurately determining fuel density.

FIG. 2 illustrates a flow diagram of method 50 for accurately determining fuel 12 density. To begin, dielectric constant versus density characteristics of fuel 12 can be obtained.

In one embodiment, steps 52, 54, and 56 can be used to obtain dielectric constant versus density characteristics at the first location. The first location will be discussed here as fuel tank 14, but in other embodiments other locations suitable for obtaining dielectric constant versus density characteristics can be used. Both density $D_1$ and dielectric constant $K_1$ of fuel 12 are measured at fuel tank 14 (step 52). Density $D_1$ of fuel 12 can be measured at fuel tank 14 using density sensor 16 and the dielectric constant $K_1$ of fuel 12 can be measured at fuel tank 14 using dielectric sensor 18, as described with respect to FIG. 1A. Density $D_1$ and dielectric constant $K_1$ measured at fuel tank 14 can then be used as values for D and K in the expression (I).

Based on the measured $D_1$ and $K_1$ values at fuel tank 14, a regression line for a plot of dielectric constant versus density can be established for the particular fuel 12 (step 54). $D_1$ and $K_1$ establish a point on the plot of dielectric constant versus density and the regression line is generated from the expression (I) so as to pass through the point $D_1$, $K_1$ by adjusting values of A and B in the expression (I). In other words, values of constants $A_1$ and $B_1$ in the expression (I) can be selected as a function of the regression line passing through the point $D_1$, $K_1$ (step 56). At this point, all variables in expression (I) have suitable values. Thus, dielectric constant versus density characteristics of fuel 12 at a first location (e.g. fuel tank 14) have been determined.

Next, a dielectric constant $K_2$ of fuel 12 can be measured at a second location (step 58). The second location can be, for example, portion 20A of fuel line 20 where environmental conditions include higher temperatures and pressures than the first location (e.g. fuel tank 14). In further embodiments, the second location can be selected as any other desired location remote from the first location and which is subjected to environmental conditions differing from environmental conditions at the first location. At a location such as portion 20A, the environmental conditions can be too extreme to permit use of a densitometer or other type of density sensor to directly measure density of fuel 12. The dielectric constant $K_2$ can be measured within portion 20A downstream of metering valve 30 using device 32 as described with respect to FIGS. 1B and 1C.

Once fuel 12 dielectric constant $K_2$ has been measured at portion 20A, density $D_2$ of fuel 12 at portion 20A can be accurately inferred (step 60). In the expression (I), dielectric constant $K_2$ of fuel 12 at portion 20A can be used as K along with the selected values of $A_1$ and $B_1$ as a function of the regression line to solve the expression for $D_2$. The expression would look as follows:

$$D_2 = \frac{K_2 - 1}{A_1(K_2 - 1) + B_1}$$

In other words, density $D_2$ of fuel 12 is inferred at portion 20A using the measured dielectric constant $K_2$ of fuel 12 at portion 20A and the dielectric constant versus density characteristics of fuel 12 determined at the first location. This provides an accurate value for density $D_2$ of fuel 12 at portion 20A independent of a temperature.

Finally, engine 22 control can be adjusted based on the accurate measurement of density $D_2$ of fuel 12 at portion 20A (step 62). Importantly, the ability to accurately measure density $D_2$ independent of temperature at portion 20A is significant because this location is where a value of fuel 12 density is most critical for use in efficient engine 22 control. Even slight inaccuracies in the value of fuel 12 density at portion 20A can result in substantial inefficiencies in engine 22 control. With an accurate value of the density of fuel 12 and the volumetric flow of fuel 12, obtained from metering valve 30, a mass flow of fuel 12 at portion 20A can be calculated and used in engine 22 control.

Discussion of Possible Embodiments

The following are non-exclusive descriptions of possible embodiments of the present invention.

A method for accurately determining a density of a fuel, the method comprising: obtaining dielectric constant versus density characteristics of the fuel at a first location; measuring a dielectric constant of the fuel at a second location, wherein environmental conditions at the second location differ from environmental conditions at the first location; and inferring the density of the fuel at the second location using the dielectric constant of the fuel at the second location and the dielectric constant versus density characteristics of the fuel at the first location.

The method of the preceding paragraph can optionally include, additionally and/or alternatively, the following techniques, steps, features and/or configurations:

The dielectric constant versus density characteristics of the fuel at the first location are obtained in accordance substantially with the following expression:

$$D = \frac{K - 1}{A(K - 1) + B}$$

where D is the density of the fuel, K is the dielectric constant of the fuel, and A and B are constants based on the type of fuel.

Obtaining the dielectric constant versus density characteristics of the fuel at the first location comprises: measuring a density of the fuel at the first location; using the density measured at the first location as D in the expression; measuring a dielectric constant of the fuel at the first location; using the dielectric constant measured at the first location as K in the expression; establishing a regression line for a plot of dielectric constant versus density based on measured values of density and dielectric constant at the first location; and selecting values of constants A and B as a function of the regression line.

Inferring the density of the fuel at the second location using the dielectric constant of the fuel at the second location and the dielectric constant versus density characteristics of the fuel at the first location comprises: using the measured dielectric constant of the fuel at the second location as the dielectric constant of the fuel K in the expression; and using the selected values of constants A and B as the constants A and B in the expression.

Passing fuel from the first location to the second location, wherein the environmental conditions at the first location include a temperature less than a temperature of the environmental conditions at the second location.

The dielectric constant of the fuel at the second location is measured by passing fuel from the first location through a gap between concentric electrode plates at the second location.

Obtaining dielectric constant versus density characteristics of the fuel at a first location comprises obtaining dielectric constant versus density characteristics of the fuel in a fuel tank external to an engine.

Determining the density of the fuel at the second location comprises determining the density of the fuel at or near a fuel metering valve in a fuel line within an engine.

Adjusting engine control based on the determination of the density of the fuel at or near the fuel metering valve.

Measuring the dielectric constant of the fuel at the second location comprises measuring the dielectric constant of the fuel passing through a fuel line within an engine downstream of a fuel metering valve.

An assembly used for determining a density of a fuel, the assembly comprising: a fuel line through which a fuel is passed and located at least partially within an engine; a fuel metering valve located within the fuel line and configured to receive the fuel through a first end and dispel the fuel through a second end; and a multi-plate capacitor device located within the fuel line through which the fuel passes, the device comprising: a first current sensing electrode plate; a second voltage driven electrode plate configured concentrically around the first plate; and an insulating material configured concentrically between the first plate and the second plate, wherein the insulating material is present in an angular range between the first plate and the second plate less than 360° such that at least one gap is defined radially between the first plate and the second plate and along an axial distance of the first plate and the second plate, and wherein the at least one gap receives fuel at an upstream end and dispels fuel at a downstream end such that a first measurement of capacitance of the fuel can be obtained across the at least one gap.

The assembly of the preceding paragraph can optionally include, additionally and/or alternatively, any one or more of the following features, configurations and/or additional components:

The device is configured such that the upstream end of the at least one gap receives fuel from the second end of the fuel metering valve.

The at least one gap has a cross-sectional area at any axial location along the gap large enough to pass debris through and small enough to slow down a flow of fuel relative to a flow of fuel passing through the fuel line and bypassing the gap.

A fuel tank located external to the engine containing a portion of the fuel; the fuel line in fluid communication with the fuel tank to deliver fuel from the fuel tank to the fuel metering valve located within the fuel line; a density sensor located at least partially within the fuel tank; and a dielectric sensor located at least partially within the fuel tank to obtain a second measurement of capacitance of the fuel.

Environmental conditions at the multi-plate capacitor device which include a temperature greater than a temperature at the fuel tank and a pressure greater than a pressure at the fuel tank.

Any relative terms or terms of degree used herein, such as "generally", "substantially", "approximately", and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, temporary alignment or shape variations induced by operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. An assembly used for determining a density of a fuel, the assembly comprising:
   a density sensor located at a first location, wherein the density sensor is configured to measure a density of the fuel at the first location;
   a first dielectric sensor located at the first location, wherein the first dielectric sensor is configured to measure a dielectric constant of the fuel at the first location;
   a second dielectric sensor located at a second location downstream of the first location, wherein environmental conditions at the second location differ from environmental conditions at the first location and wherein the second dielectric sensor is configured to measure a dielectric constant of the fuel at the second location; and
   a fuel line connecting the first location to the second location;
   wherein the density of the fuel at the second location is inferred based on the measured density and dielectric constant at the first location, the measured dielectric constant at the second location, and dielectric versus density characteristics of the fuel at the first location.

2. The assembly of claim 1, wherein the dielectric constant versus density characteristics of the fuel at the first location are obtained in accordance substantially with the following expression:

$$D = \frac{K-1}{A(K-1)+B}$$

where D is the density of the fuel, K is the dielectric constant of the fuel, and A and B are constants based on the type of fuel.

3. The assembly of claim 2, wherein obtaining the dielectric constant versus density characteristics of the fuel at the first location comprises:
   using the density measured at the first location as D in the expression and
   using the dielectric constant measured at the first location as K in the expression;
   establishing a regression line for a plot of dielectric constant versus density based on measured values of density and dielectric constant at the first location; and
   selecting values of constants A and B as a function of the regression line.

4. The assembly of claim 3, wherein the density of the fuel at the second location is inferred by:

using the measured dielectric constant of the fuel at the second location as the dielectric constant of the fuel K in the expression; and using the selected values of constants A and B as the constants A and B in the expression.

5. The assembly of claim 1,
wherein the environmental conditions at the first location include a temperature less than a temperature of the environmental conditions at the second location.

6. The assembly of claim 5, wherein the dielectric sensor at the second location comprises a gap between concentric electrode plates, and wherein the dielectric constant at the second location is measured by passing fuel from the first location through the gap.

7. The assembly of claim 1, wherein the first location is in a fuel tank external to an engine.

8. The assembly of claim 7, wherein the second location is at or near a fuel metering valve in the fuel line, wherein the fuel metering valve is within an engine.

9. The assembly of claim 8,
wherein the determination of the density of the fuel at or near the fuel metering valve is used to adjust engine control.

10. The assembly of claim 7, wherein the second location is downstream of a fuel metering valve in the fuel line, wherein the metering valve is within an engine.

11. An assembly used for determining a density of a fuel, the assembly comprising:
a density sensor located at a first location, wherein the density sensor is configured to measure a density of the fuel at the first location;
a dielectric sensor located at the first location, wherein the dielectric sensor is configured to measure a dielectric constant of the fuel at the first location;
a fuel line through which a fuel from the first location is passed, wherein the fuel line is located at least partially within an engine;
a fuel metering valve located within the fuel line and configured to receive the fuel through a first end and dispel the fuel through a second end; and
a multi-plate capacitor device located within the fuel line through which the fuel passes, the device comprising:
a first current sensing electrode plate;
a second voltage driven electrode plate configured concentrically around the first plate; and
an insulating material configured concentrically between the first plate and the second plate, wherein the insulating material is present in an angular range between the first plate and the second plate less than 360° such that at least one gap is defined radially between the first plate and the second plate and along an axial distance of the first plate and the second plate, and wherein the at least one gap receives fuel at an upstream end and dispels fuel at a downstream end such that a first measurement of capacitance of the fuel can be obtained across the at least one gap.

12. The assembly of claim 11, wherein the device is configured such that the upstream end of the at least one gap receives fuel from the second end of the fuel metering valve.

13. The assembly of claim 11, wherein the at least one gap has a cross-sectional area at any axial location along the gap large enough to pass debris through and small enough to slow down a flow of fuel relative to a flow of fuel passing through the fuel line and bypassing the gap.

14. The assembly of claim 11, wherein the first location is a fuel tank located external to the engine and containing a portion of the fuel, wherein the density sensor and the dielectric sensors are located at least partially within the fuel tank, and wherein the fuel line is in fluid communication with the fuel tank to deliver fuel from the fuel tank to the fuel metering valve located within the fuel line.

15. The assembly of claim 11, further comprising environmental conditions at the multi-plate capacitor device which include a temperature greater than a temperature at the fuel tank and a pressure greater than a pressure at the fuel tank.

* * * * *